United States Patent [19]

Ludec

[11] 4,291,178

[45] Sep. 22, 1981

[54] PREPARATION OF ORTHO-HYDROXYBENZYL ALCOHOLS

[75] Inventor: Joël L. Ludec, Lyons, France

[73] Assignee: Rhone-Poulenc Industries, Paris, France

[21] Appl. No.: 55,071

[22] Filed: Jul. 5, 1979

[30] Foreign Application Priority Data

Jul. 11, 1979 [FR] France .................. 78 21591

[51] Int. Cl.$^3$ .................. C07C 37/00; C07C 27/00
[52] U.S. Cl. .................. 568/764
[58] Field of Search .................. 568/764

[56] References Cited

U.S. PATENT DOCUMENTS

| | | | |
|---|---|---|---|
| 3,290,352 | 12/1966 | Marchand | 568/764 |
| 3,290,393 | 12/1966 | Marchand | 568/764 |
| 3,297,737 | 1/1967 | Weck | 568/764 |
| 4,025,553 | 5/1977 | Nagatu et al. | 568/764 |

FOREIGN PATENT DOCUMENTS

| | | | |
|---|---|---|---|
| 1338945 | 4/1963 | France | 568/764 |
| 2132861 | 4/1972 | France | 568/764 |

*Primary Examiner*—Werren B. Lone
*Attorney, Agent, or Firm*—Burns, Doane, Swecker & Mathis

[57] ABSTRACT

A yield improved process for the preparation of orthohydroxybenzyl alcohols by esterifying a phenol with boric acid, next condensing the product of esterification with either formaldehyde or a formaldehyde-generating compound, thus effecting formulation of a boric acid ester of the desired ortho-hydroxybenzyl alcohol, and thence decomposing said ester to liberate the ortho-hydroxybenzyl alcohol therefrom, the improvement which comprises preparing the boric acid/phenol esters from at least 1.1 mols of the phenol per mol of boric acid.

14 Claims, No Drawings

PREPARATION OF ORTHO-HYDROXYBENZYL ALCOHOLS

BACKGROUND OF THE INVENTION

1. Field of the Invention:

The present invention relates to the preparation of ortho-hydroxybenzyl alcohols, and, more especially, to the preparation of ortho-hydroxybenzyl alcohol, commonly known as saligenol, by the condensation of either formaldehyde or a formaldehyde-generating compound with esters derived from boric acid and from phenol or substituted phenols.

2. Description of the Prior Art:

Ortho-hydroxybenzyl alcohols are desirable intermediates for the preparation of the ortho-hydroxymethyl-phenylacetic acids which are useful as plant growth regulators. Saligenol itself is an important industrial product both for its pharmacological properties and as an intermediate for the synthesis of insecticides.

The presently most valuable industrial process for the manufacture of ortho-hydroxybenzyl alcohols consists of reacting formaldehyde or one of its derivatives with an aryl metaborate; compare U.S. Pat. Nos. 3,290,352 and 3,290,393 and French Pat. No. 1,328,945, each hereby expressly incorporated by reference in its entirety and relied upon. This process provides saligenol in yields on the order of 65%, expressed relative to the phenol and the formaldehyde employed in the reaction. Despite its value, it has been determined that this process is not without disadvantages from an economic point of view. In fact, in a process of this kind, the formaldehyde which is not converted to saligenol is lost in the form of by-products and/or cannot be recovered from the reaction mixture. And insofar as the boric acid is concerned, although same is not converted in the reaction process, it too is lost because the recovery of same would require the use of expensive isolation techniques. The loss of these two products consequently contributes to an increase in the cost of saligenol.

SUMMARY OF THE INVENTION

Accordingly, a major object of the present invention is to avoid the disadvantages of the process described in the aforesaid U.S. Pat. Nos. 3,290,352 and 3,290,393, and the French Pat. No. 1,328,945 and, more particularly, to provide an improved process characterized by enhanced yields of ortho-hydroxybenzyl alcohols, relative to the phenol and the formaldehyde, and by enhanced efficacy relative to the boric acid employed.

More specifically, the present invention features an improved process for the preparation of ortho-hydroxybenzyl alcohols by reacting esters of boric acid and of phenols with formaldehyde or a formaldehyde-generating substance, thus effecting the in situ formation of the boric acid esters of ortho-hydroxybenzyl alcohols, and thence decomposing said latter esters in order to liberate the subject ortho-hydroxybenzyl alcohols, and which process is characterized in that the boric acid esters of the phenols employed for the condensation are obtained by reacting at least 1.1 mols of the phenol with one mol of boric acid.

DETAILED DESCRIPTION OF THE INVENTION

It has now surprisingly been found that the use, for the condensation with formaldehyde, of boric acid esters of phenols obtained by reacting at least 1.1 mols of a phenol with 1 mol of boric acid enables substantial improvement in the yields of the product ortho-hydroxybenzyl alcohols, relative to the phenol converted, and considerably enhances the yield of hydroxybenzyl alcohols, relative to the formaldehyde employed in the reaction. This results in a simultaneous decrease in the consumption of boric acid per kilogram of benzyl alcohols manufactured.

The boric acid esters of phenols obtained by reacting at least 1.1 mols of the phenol with 1 mol of boric acid, which esters will hereafter be referred to as the "aryl borates" for purposes of convenience, are complex mixtures comprising:

Phenol metaborates having the structural formula:

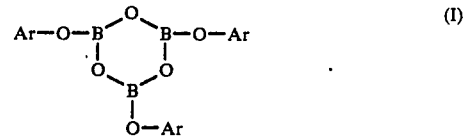  (I)

Phenol pyroborates:

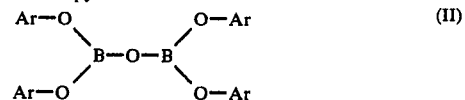  (II)

Phenol orthoborates:
  (III)

and

Phenol acid borates:
  (IV)

(in which formulae Ar represents a substituted or unsubstituted phenyl radical, as more fully defined below), which mixtures optionally contain excess phenol. The proportion of each of the aforesaid boric acid derivatives in the esterification mixture obviously varies as a function of the molar ratio of phenol/boric acid and/or as a function of the degree of esterification. Thus, for molar ratios of phenol/boric acid of between 1.1 and 1.5, the mixture mainly comprises metaborates, and, for ratios which are equal to or on the order of 3, the orthoborates are virtually the only components of the mixture. When preparing the aryl borates, it was found that it was not necessary to convert all the phenol employed to borate, in particular if the molar ratio of phenol/boric acid is on the order of 3, in order to obtain good yields of ortho-hydroxybenzyl alcohols; it is therefore possible to limit the degree of esterification of the phenol in question, but without such degree being less than 70%, and preferably 80%, of the phenol employed. In this case, a mixture of aryl borates is obtained which contains the unconverted phenol, the acid borates of the formula (IV) and the aryl orthoborate.

The aryl borates are prepared consistent with known processes, by reacting a phenol with boric acid in a solvent which forms an azeotrope with the water evolved during esterification reaction. The latter is removed by azeotropic distillation as it is formed. Aromatic hydrocarbons, such as benzene, toluene and xylene, are representative of suitable solvents for the preparation of the aryl borates. Any other inert solvent which permits the azeotropic distillation of the water can be used.

The condensation of the formaldehyde with the aryl borate can be carried out directly on the anhydrous aryl borate solution thus obtained, optionally after dilution with an additional amount of the solvent selected. The amount of formaldehyde employed is preferably 1 mol per mol of boric acid, although it is possible to deviate to some extent from this proportion (same can be, for example, between 0.9 and 1.1 mols per mol of boric acid), but without any particular advantage being gained thereby. If a formaldehyde generator is used (for example formaldehyde oligomers or polymers), the amount is obviously calculated such that the amount of formaldehyde available for the reaction is 1 mol per mol of boric acid.

The phenyl borate/formaldehyde condensation could be carried out in a different solvent from that utilized in the stage of preparation of the aryl borate, without departing from the ambit of the present invention, but this complicates the process without providing any particular advantage.

The temperature for the condensation of the formaldehyde, or its generator, with the phenol can be between 20° and 120° C., and preferably between 40° and 100° C.

The condensation reaction mixture is a complex mixture of ortho-hydroxybenzyl alcohol borates and mixed aryl/ortho-hydroxybenzyl alcohol borates, the composition of which varies with the compositions of the mixture of aryl borates selected as the starting material. Regardless of the composition of this reaction mixture, the liberation of the ortho-hydroxybenzyl alcohols from the condensation products can be carried out in accordance with those processes described in the U.S. Pat. Nos. 3,290,352 and 3,290,393, and the French Pat. No. 1,328,945, namely, by saponification, alcoholysis or hydrolysis. The saponification process is very particularly suitable because it makes it possible, especially in those cases where the ratio of phenol/boric acid becomes large, to easily recover the excess phenols which can be recycled to a further operation for the preparation of aryl borates. This technique is very especially attractive if the ratio of phenol/boric acid is between 1.5 and 3, this involving the recovery of the phenols. In order to successfully carry out such a recovery of the phenol and the separation thereof from the ortho-hydroxybenzyl alcohols, it is important, in a first step, to conduct the saponification with an amount of alkaline agent in aqueous solution (in particular, sodium hydroxide or potassium hydroxide in aqueous solution) which is calculated such as to effect formation, from the ortho-hydroxybenzyl alcohol borates, of the complexes of the formula:

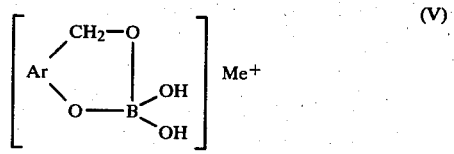

(V)

in which Me represents an alkali metal, which complexes are water-soluble, without giving rise to the formation of alkali metal phenates from the phenols liberated during the saponification. Under these conditions, the phenols liberated remain in solution in the organic solvent employed during the esterification and condensation stage, and the complex salt of the formula (V), derived from the ortho-hydroxybenzyl alcohol formed, transfers into the aqueous phase. The organic and aqueous phase are then separated by decantation. The organic phase containing the excess phenol can be directly re-used for a further operation. In a second step, the aqueous phase can in turn be treated in various ways in order to liberate the ortho-hydroxybenzyl alcohol from the complex of the formula (V). For example, the aqueous solution can be treated with an inorganic acid or the ortho-hydroxybenzyl alcohol can be displaced via the action of a compound having a greater complexing power than that of said alcohol, for example, a polyol, such as mannitol and sorbitol, which form very water-soluble complexes with boric acid; the ortho-hydroxybenzyl alcohols liberated are extracted with a suitable solvent. After separation of the organic phase containing the phenol, it is also possible to treat the aqueous phase with an aqueous alkaline solution to liberate the ortho-hydroxybenzyl alcohol in the form of an alkali metal salt thereof. In this case, an aqueous solution of alkali metal borate and of alkali metal salt of the ortho-hydroxybenzyl alcohol is recovered; the alcohol can be recovered from this solution by extraction, after acidification, or the solution can be directly used for the preparation of ortho-hydroxybenzyl alcohol derivatives. For example, the ortho-hydroxybenzyl alcohols, in the form of their alkali metal salts, can be oxidized with oxygen or air to provide the corresponding hydroxybenzaldehydes.

The amount of alkali metal base to be employed in the first saponification step, in order to separate off the excess phenol at the completion of the aryl borate/formaldehyde condensation, is at most 1.2 mols per mol of boric acid, preferably 1 mol per mol and at least 0.8, and preferably 0.9, mol of alkali metal base per mol of boric acid. The "suitable amount" can easily be determined in each particular case by simple experimentation.

The amount of alkali metal base employed in the second saponification step is typically between 0.8 and 1.5 mols per mol of boric acid initially employed.

The phenols which are suitable for conducting the process of the present invention are represented by the structural formula:

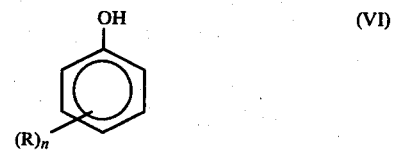

(VI)

in which n is an integer from 1 to 3 and R represents: an alkyl radical having from 1 to 12, and preferably from 1 to 4 carbon atoms, such as methyl, ethyl, propyl, butyl, hexyl and octyl; an alkoxy radical having from 1 to 12, and preferably from 1 to 4 carbon atoms, such as the methoxy, ethoxy, propoxy and butoxy groups; or a halogen atom such as chlorine and bromine. If n is greater than 1, at least one of the ortho-positions relative to the phenolic hydroxy group must be free of any substituents. The phenols of the formula (VI) enable synthesis of ortho-hydroxybenzyl alcohols of the general formula

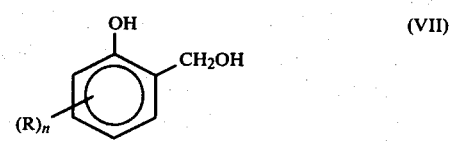

(VII)

in which R and n are as above defined.

Examples of phenols of the formula (VI) which are representative are phenol, cresols, 2,3-xylenol, 3,4-xylenol, monoethylphenols, 2-methoxyphenol, 3-methoxyphenol, 4-methoxyphenol, 2,3-dimethoxyphenol, 2-ethoxyphenol, 4-ethoxyphenol and monochlorophenols.

The process according to the invention is very particularly suitable for the preparation of saligenol from phenol.

In order to further illustrate the present invention and the advantages thereof, the following specific examples are given, it being understood that same are intended only as illustrative and in no wise limitative.

EXAMPLE 1

155.92 g of 98.6% pure phenol (1.634 mols), 33.48 g of 100% pure boric acid (0.542 mol) and 40 ml of toluene were introduced into a 1,000 ml glass round-bottomed flask equipped with a central stirrer, a thermometer, heating means and a system for separating off the water entrained by azeotropic distillation, and the mixture was heated at its boiling point, and under stirring, until the amount of water removed by azeotropic distillation corresponded to 82% of the amount of water resulting from complete esterification. The temperature in the reaction mixture attained a value of 160° C.

After cooling to about 100°, the toluene solution thus obtained, which contained essentially phenyl orthoborate, was diluted with 200 ml of anhydrous toluene and then heated to 90° C.

Paraformaldehyde (16.94 g of 95.9% pure material, i.e., 0.542 mol) was then introduced over the course of 30 minutes and stirring was continued at the same temperature for 1 hour 30 minutes.

The reaction mixture was subsequently cooled to about 20° and then run into ice-cold water (290 g) over the course of 20 minutes, while stirring same thoroughly. 123.16 g of dilute sodium hydroxide solution of 17.59% strength by weight (i.e., 0.542 mol of NaOH) were added to this mixture and the resulting mixture was stirred for 20 minutes at ambient temperature. Stirring was discontinued and the mixture was then left to separate.

The upper toluene phase was recovered.

The aqueous phase was washed with toluene (2 times, 100 ml).

The toluene layers were combined; same contain the excess phenol, namely, 1.087 mols, which was determined by liquid phase chromatography. The degree of conversion of the phenol, therefore, was 33.5%.

165.05 g of an aqueous sodium hydroxide solution of 17.59% strength by weight (i.e., 0.72 mol of NaOH) were added to the aqueous phase from which the phenol had been removed; this solution contained sodium borate and sodium saligenate which was determined by liquid phase chromatography in a column having an internal diameter of 4 mm and a length of 15 cm, which was packed with an octadecyl trimethoxy silane grafted onto silica phase, having a particle size of 5 mm (a product marketed by Société MERCK under the designation RP 18). The eluant consisted of an aqueous alcoholic solution obtained by mixing 25% by volume of ethanol and 75% by volume of an aqueous solution, buffered to pH=3.4, which was obtained by diluting to 1,000 ml a mixture of 0.923 g of sodium acetate trihydrate and 7 ml of acetic acid. In this manner, 0.528 mol of saligenol was determined and this corresponded to a yield of 97.6%, relative to the formaldehyde employed. The yield relative to the uncovered phenol was 97%.

EXAMPLES 2 to 4

Example 1 was repeated, the molar ratio of phenol/boric acid being varied. The following results were obtained:

| EXAMPLE | Phenol/H$_3$BO$_3$ | Degree of conversion of phenol % | Yield of saligenol/formaldehyde employed % | Yield of saligenol/unrecovered phenol % |
|---|---|---|---|---|
| 2 | 1.2 | 79 | 82.5 | 87 |
| 3 | 1.5 | 67 | 91.4 | 91 |
| 4 | 2 | 51.5 | 93.3 | 90.6 |

Note:
The degree of esterification was 97, 93 and 98% in Examples 2, 3 and 4, respectively.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a process for the preparation of an orthohydroxybenzyl alcohol by (a) reacting a phenol with boric acid to form boric acid esters of said phenol, (b) condensing said boric acid esters with formaldehyde or a formaldehyde-generating compound to form the corresponding ortho-hydroxybenzyl alcohol boric acid esters, and then (c) decomposing said orthohydroxybenzyl alcohol boric acid esters to liberate the corresponding ortho-hydroxybenzyl alcohol therefrom the improvement comprising employing the reactants in step (a) in a ratio of at least 1.1 mols of said phenol per mol of boric acid to form in step (a) boric acid esters of said phenol which comprise phenol orthoborates.

2. A process as defined in claim 1 wherein the phenol reactant employed in step (a) has the structural formula

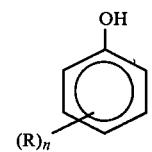

wherein n is 0, 1, 2 or 3 and R is an alkyl radical having from 1 to 12 carbon atoms, an alkoxy radical having from 1 to 12 carbon atoms or a halogen atom at least one of the ortho-positions relative to the phenolic hydroxyl being free when n is 2 or 3, said process affording the corresponding ortho-hydroxybenzyl alcohol product having the structural formula

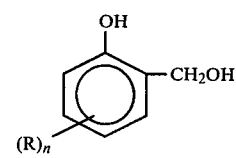

wherein n and R are defined as above.

3. A process as defined in claim 1 or 2 wherein the reactants in step (a) are employed in a ratio of from about 1.2 to about 3 mols of said phenol per mol of boric acid.

4. A process as defined by claim 1 wherein the reactants in step (a) are employed in a ratio of from about 1.5 to about 3 mols of said phenol per mol of boric acid.

5. A process as defined by claim 1 wherein the ortho-hydroxybenzyl alcohol boric acid esters are decomposed from a solvent solution thereof, said solvent also comprising a phenol/boric acid solvent of esterification.

6. A process as defined by claim 5, said solvent being an aromatic hydrocarbon.

7. A process as defined by claim 1 or 5, wherein the amount of formaldehyde employed in step (b) is about 1 mol per mol of boric acid.

8. A process as defined in claim 1, wherein the temperature employed for the formaldehyde condensation step (b) is between about 20° and about 120° C.

9. A process as defined in claim 7, wherein an organic solvent is employed during steps (a) and (b) and wherein excess phenol is separated from the ortho-hydroxybenzyl alcohol by treating the reaction mixture obtained at the end of step (b) with an aqueous solution of an alkali metal base, in an amount of from about 0.8 to about 1.2 mols of alkali metal base per mol of boric acid, to form a complex alkali metal salt of the orthohydroxybenzyl alcohol boric acid esters, followed by separation by decantation of the organic phase containing said phenol from the aqueous phase containing the complex and liberation of the ortho-hydroxybenzyl alcohol from its complex.

10. A process is defined by claim 9, wherein the amount of alkali metal base employed is between about 0.9 and about 1.1 mols per mol of boric acid.

11. A process as defined by claim 9, wherein the amount of alkali metal base employed is about 1 mol per mol of boric acid.

12. A process as defined by claim 10, wherein the alkali metal base employed is sodium hydroxide or potassium hydroxide.

13. A process as defined by claim 10, wherein the ortho-hydroxybenzyl alcohol is liberated by treating the aqueous phase containing the complex with an alkali metal base to afford an aqueous solution of alkali metal borate and of alkali metal salt of the ortho-hydroxybenzyl alcohol.

14. A process as defined by claim 1 for the preparation of saligenol, wherein phenol and boric acid are reacted in a ratio of from at least 1.1 to about 3 mols of phenol per mol of boric acid, in an organic solvent which forms an azeotrope with the water of esterification, said water being removed by azeotropic distillation; a solution in an organic solvent of the phenyl borate thus formed is then condensed with formaldehyde or a formaldehyde generator, in an amount of about 1 mol of formaldehyde per mol of boric acid, at a temperature of between about 20° and about 120° C.; the reaction mixture obtained after condensation is then treated with an aqueous solution of from about 0.8 to about 1.2 mols of an alkali metal base per mol of boric acid, to form a complex alkali metal salt of saligenol and of boric acid; the resultant organic phase containing excess phenol is separated from the aqueous phase containing the complex alkali metal salt of saliginol and of boric acid; and the aqueous phase containing said complex is treated with an aqueous solution of an alkali metal base, saligenol being liberated therefrom in the form of its alkali metal saligenate.

* * * * *

UNITED STATES PATENT AND TRADEMARK OFFICE
CERTIFICATE OF CORRECTION

PATENT NO. : 4,291,178

DATED : September 22, 1981

INVENTOR(S) : Joel Le Ludec

It is certified that error appears in the above—identified patent and that said Letters Patent are hereby corrected as shown below:

On the Title page,

The inventor's name should read -- Joel Le Ludec --.

Signed and Sealed this

Seventh Day of September 1982

[SEAL]

Attest:

*Attesting Officer*

GERALD J. MOSSINGHOFF

*Commissioner of Patents and Trademarks*